(12) United States Patent
Mitsui

(10) Patent No.: US 10,722,401 B2
(45) Date of Patent: Jul. 28, 2020

(54) CONTACT LENS FOR CORRECTIVE CORNEAL CROSSLINKING AND METHOD FOR PRODUCING SAME

(71) Applicant: MITSUI MEDICAL COMMERCE CO., LTD., Tokyo (JP)

(72) Inventor: Iwane Mitsui, Tokyo (JP)

(73) Assignee: MITSUI MEDICAL COMMERCE CO, LTD., Tokyo (JP)

( * ) Notice: Subject to any disclaimer, the term of this patent is extended or adjusted under 35 U.S.C. 154(b) by 0 days.

(21) Appl. No.: 16/063,830

(22) PCT Filed: Dec. 22, 2016

(86) PCT No.: PCT/JP2016/088392
§ 371 (c)(1),
(2) Date: Jun. 19, 2018

(87) PCT Pub. No.: WO2017/111027
PCT Pub. Date: Jun. 29, 2017

(65) Prior Publication Data
US 2019/0008683 A1 Jan. 10, 2019

(30) Foreign Application Priority Data
Dec. 22, 2015 (JP) ................................. 2015-250664

(51) Int. Cl.
*A61F 9/013* (2006.01)
*A61N 1/30* (2006.01)
(Continued)

(52) U.S. Cl.
CPC .............. *A61F 9/013* (2013.01); *A61F 2/142* (2013.01); *A61N 1/30* (2013.01); *A61N 1/325* (2013.01);
(Continued)

(58) Field of Classification Search
CPC .......... A61F 2/142; A61F 2/145; A61F 2/147; A61F 9/013; A61K 9/0048; A61K 9/0051;
(Continued)

(56) References Cited

U.S. PATENT DOCUMENTS 6,582,077 B1 * 6/2003 Tabb ..................... G02C 7/047
351/159.74
2016/0354239 A1 * 12/2016 Roy ....................... A61F 9/0017

FOREIGN PATENT DOCUMENTS

JP H07-500267 A 1/1995
JP 2013-066624 A 4/2013
(Continued)

OTHER PUBLICATIONS

Package Insert. Boston(R) EQUALENS(R) II (oprifocon A). Polymer Technology, a Bausch & Lomb Company. Printed Jan. 2004. Accessed Aug. 12, 2019. (Year: 2004).*
(Continued)

*Primary Examiner* — William R Carpenter
*Assistant Examiner* — Larry R. Wilson
(74) *Attorney, Agent, or Firm* — Oliff PLC

(57) ABSTRACT

A contact lens for corrective corneal crosslinking has a lens part and reservoir part. The lens part is constituted of a UV transmitting material, and provided, on a side thereof being in contact with the cornea of a patient's eyeball, with a pressing region configured to project in a convexly curved shape at a position for pressing the corneal dome center, and a relief region including an annular concave part whose cross section has a concavely circular arc shape that surrounds the pressing region's outer circumference. The reservoir part is disposed seamlessly and integrally therewith on the lens' outer side in a thickness direction in the pressing region, the reservoir part is provided with a communication
(Continued)

hole for communication between the inside of the reservoir part and the pressing region, and a working electrode that has the same polarity as that of the riboflavin solution in the reservoir part.

16 Claims, 6 Drawing Sheets

(51) Int. Cl.
    *G02C 7/04*     (2006.01)
    *A61N 1/36*     (2006.01)
    *A61N 1/32*     (2006.01)
    *A61F 2/14*     (2006.01)
    *A61F 9/008*     (2006.01)

(52) U.S. Cl.
    CPC ........... *A61N 1/36046* (2013.01); *G02C 7/04* (2013.01); *A61F 2009/00872* (2013.01)

(58) Field of Classification Search
    CPC ...... A61N 1/325; A61N 1/36046; A61N 1/30; G02C 7/04; G02C 7/047; G02C 7/083; G02C 7/085
    See application file for complete search history.

(56) References Cited

FOREIGN PATENT DOCUMENTS

| | | |
|---|---|---|
| JP | 2013-521988 A | 6/2013 |
| JP | 2015-036080 A | 2/2015 |
| JP | 5828535 B1 | 12/2015 |
| WO | 2009/090763 A1 | 7/2009 |
| WO | 2014/210152 A2 | 12/2014 |

OTHER PUBLICATIONS

Jun. 12, 2019 European Search Report issued in European Patent Application No. 16878914.7.
Apr. 4, 2017 International Search Report issued in International Patent Application No. PCT/JP2016/088392.
Jan. 10, 2018 International Preliminary Report on Patentability issued in International Patent Application No. PCT/JP2016/088392.

\* cited by examiner

CONTACT LENS FOR CORRECTIVE CORNEAL CROSSLINKING AND METHOD FOR PRODUCING SAME

TECHNICAL FIELD

The present invention relates to a contact lens for corrective corneal crosslinking and a method for producing the same. The contact lens for corrective corneal crosslinking changes the corneal shape of a patient while being mounted for a given period of time, and allows, when myopia, hyperopia, or keratoconus cornea is corrected, infiltration of a riboflavin (vitamin B2) solution into a corneal tissue and UV irradiation for crosslinking collagens constituting the cornea, thereby enhancing the corneal strength and fixing the cornea.

BACKGROUND ART

A contact lens under development is of a type that is mounted, for example, during sleep and changes the corneal shape of a patient, thereby correcting myopia, hyperopia, and/or astigmatism while the contact lens is removed.

When the above-described contact lens is not mounted for a long period of time, the restoring force of the cornea restores the original myopia or hyperopia state. It is thus desirable to fix the cornea in a corrected state.

On the other hand, in a refraction correction surgery, while riboflavin (vitamin B2) is infiltrated, a corneal tissue is irradiated with UV rays for crosslinking collagens constituting the cornea, thereby enhancing the corneal strength and fixing the cornea.

For corneal crosslinking, a retractor is used to keep open the eye of a patient, and a riboflavin solution is dropped from a cylindrical reservoir part mounted above the cornea so as to be infiltrated into the cornea.

Also, in Patent Literature 1, the present inventor proposed a contact lens for corrective corneal crosslinking and a crosslinking method for cornea correction.

In this method, a crosslinking method and a contact lens of cornea correction are combined to fix the corneal shape in a state where the cornea is corrected by the contact lens to a certain extent.

Also in this case, infiltration of a riboflavin solution is performed in a state where the contact lens for cornea correction is removed as in the case of the above-mentioned method.

The foregoing methods have the following problems: to drop and infiltrate a riboflavin solution with the eye of a patient open, the patient is restrained by a retractor under the state of having to keep the eye opened for a long period of time (about 30 minutes); and since the dropped riboflavin solution does not completely infiltrate into the cornea and most of the solution leaks outside, a physician needs to frequently perform the task of blotting up the leaked riboflavin solution. Furthermore, when UV irradiation is performed, a contact lens is mounted after a riboflavin solution infiltrates into the cornea. The problem is that the deformation characteristics of the cornea differ from those before infiltration of the riboflavin solution, making it impossible to sufficiently correct the cornea.

As in the case of the conventional contact lens, the aforementioned contact lens for cornea correction is produced on the basis of the design concept that the thickness should be as small as possible (currently, the lens thickness at the central part is 0.14 mm or greater and 0.25 mm or smaller). Thus, the problem of the aforementioned contact lens for cornea correction is that the contact lens is likely to crack.

This contact lens for cornea correction is formed by grinding and cutting out from a circular-plate material, which is usually called a button, with a diameter of 10 mm and a height of 5 mm. In the production process thereof, one surface is first ground and cut out, and the other surface is ground while the ground and cut out surface to which a curved shape is given is supported, to form the contact lens, for example, disclosed in Patent Literature 1. The problem of this production process is that the lens material is eventually broken when the other surface is ground.

CITATION LIST

Patent Literature

Patent Literature 1: Japanese Patent Application Laid-Open No. 2015-36080

SUMMARY OF INVENTION

Technical Problem

An object of the present invention is to provide a contact lens for corrective corneal crosslinking and a method for producing the same. The contact lens for corrective corneal crosslinking with high rigidity and high crack resistance allows, while being mounted on a patient, a riboflavin solution to infiltrate into the cornea in a short period of time and UV irradiation for cornea crosslinking.

Solution to Problem

The present inventor has found that, by providing a contact lens for corrective corneal crosslinking with: a reservoir part capable of storing a riboflavin solution for corrective corneal crosslinking; a working electrode that has the same polarity as that of the riboflavin solution and is provided at a position in contact with the riboflavin solution in the reservoir part; and a communication hole for guiding the riboflavin solution in the reservoir part to the inner side of the lens, the riboflavin solution can be infiltrated quickly and reliably by iontophoresis and UV irradiation is possible while the contact lens is mounted on the cornea, that is, in a state where the cornea is corrected.

The present inventor has also found that: when the contact lens for corrective corneal crosslinking is used, the eye of a patient is kept open and the eyelids are not closed during surgery, and thus the side of the contact lens that is not in contact with the cornea may be of any shape, and a lens thickness of twice or more greater than that of a conventional contact lens is not problematic, whereby the rigidity and crack resistance of the contact lens can be increased.

Specifically, the above-described problems are solved by the following embodiments.

A contact lens for corrective corneal crosslinking, the contact lens being constituted of a UV transmitting material, the contact lens having a relief region including a concave part and a pressing region including a convex part that are formed on a side of the contact lens in contact with the cornea of a patient, the contact lens being for correcting at least one of the naked eye vision and keratoconus cornea by pressing the relief region and the pressing region to the cornea to change the shape of the cornea, the contact lens for corrective corneal crosslinking comprising a lens part and a reservoir part, wherein: the lens part has, on the side thereof being in contact with the cornea of the patient, a circular central lens region that is located at a position being in contact with a corneal dome center when the contact lens is mounted on the cornea, and a ring-shaped region in a circular-ring shape surrounding the central lens region; one of the central lens region and the ring-shaped region constitutes the pressing region or the relief region and the other constitutes the relief region or the pressing region; the reservoir part is constituted of the same material as that of the lens part, is disposed and formed to project seamlessly and integrally with the lens part at an outside position in a lens thickness direction in the central lens region, is configured to store a riboflavin solution for corrective corneal crosslinking, and has a working electrode that is disposed at a position being in contact with the riboflavin solution and has the same polarity as that of the riboflavin solution; and the lens part has a communication hole for communication between the inside of the reservoir part and the central lens region, has a lens thickness of 0.3 mm or greater and 1.0 mm or smaller in the central lens region, and enables infiltration of the riboflavin solution into a corneal tissue by iontophoresis.

(2) In the contact lens for corrective corneal crosslinking according to (1) described above, the central lens region is the pressing region configured to project in a convexly curved shape at a position for pressing the corneal dome center when the contact lens is mounted on the cornea and to form a concavely curved surface on the cornea; the ring-shaped region is the relief region that is formed at a position surrounding the outer circumference of the pressing region and includes an annular concave part whose cross section has a concavely circular arc shape; and a lens thickness of a bottom surface region of the annular concave part constituting the relief region is at least 0.3 mm.

(3) In the contact lens for corrective corneal crosslinking according to (1) described above, the central lens region is the relief region that is formed in a concavely curved shape at a position being in contact with the corneal dome center when the contact lens is mounted on the cornea, and is configured to form a convexly curved surface on the cornea, and the ring-shaped region is the pressing region that is formed at a position surrounding the outer circumference of the relief region and includes an annular convex part whose cross section has a convexly circular arc shape.

A method for producing the contact lens for corrective corneal crosslinking according to any one of (1) to (3) described above, comprising: forming the reservoir part on one end surface of a circular plate lens material; and then grinding the pressing region and the relief region on the other end surface, while the reservoir part is held, to form the lens part seamlessly and integrally with the reservoir part and a surface of the lens part to be in contact with the cornea of a patient.

Advantageous Effects of Invention

The contact lens for corrective corneal crosslinking according to the present invention allows a riboflavin solution to reliably infiltrate into the cornea of the patient in a short period of time while the aforementioned contact lens is mounted on the cornea, in other words, in a state where the cornea is corrected. Also, occurrence of crack can be restrained during grinding and cutting out as well as during use since the lens thickness at the central lens part is at least twice greater than that of the conventional lens.

In particular, when a penetration hole is formed in the lens thickness direction so that a riboflavin solution can be readily introduced to the cornea surface from outside the lens, the lens strength decreases due to formation of the penetration hole. However, a decrease in the lens strength can be compensated by increasing the lens thickness.

Also, to grind and cut out a contact lens for corrective corneal crosslinking from a lens material, when the reservoir part is first ground and cut out or is formed by an injection molding or the like in advance and then the formed reservoir part is held to grind and cut out the pressing region and the relief region, the reservoir part is thick. Since the thick reservoir part has sufficient strength, grinding and cutout of the pressing region and the relief region can be stably performed.

DESCRIPTION OF EMBODIMENTS

Figure 1:
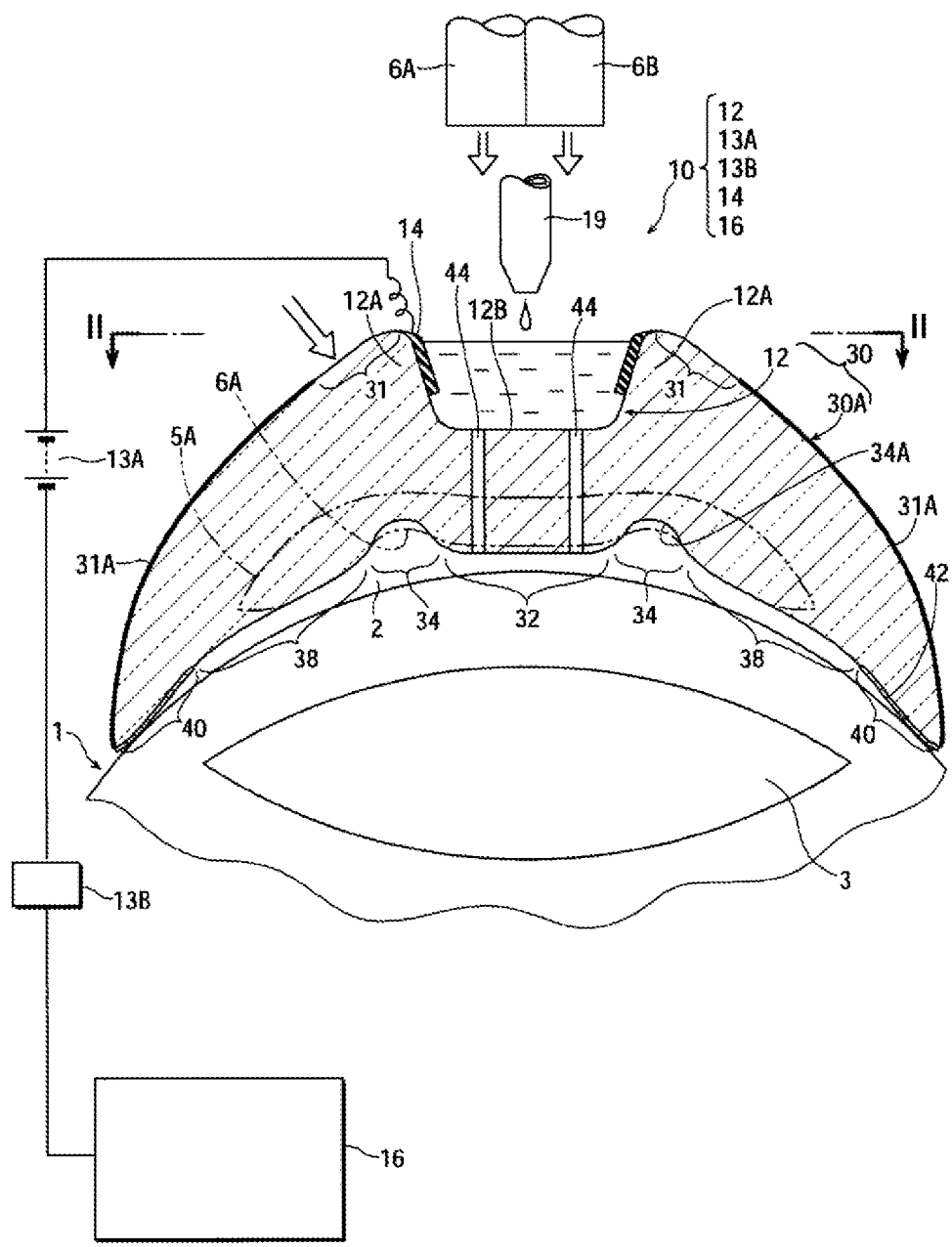
FIG. 1 is a cross-sectional view schematically illustrating a contact lens for corrective corneal crosslinking for correcting myopia according to Example 1 of the present invention.

Embodiments of the present invention will now be described.

A contact lens for corrective corneal crosslinking of this embodiment is of a thick structure where the lens thickness is 0.3 mm or greater and 1.0 mm or smaller at the lens center. In the aforementioned contact lens, a relief region constituted by a concave part and a pressing region constituted by a convex part are formed on the side in contact with the cornea of a patient. By pressing the relief region and the pressing region to the cornea so that a part of the cornea is pressed by the pressing region and a part of the cornea is projected to the relief region in reaction thereto, the corneal shape is corrected into a shape where desirable naked eye vision can be obtained or a shape where the keratoconus cornea is smoothly pressed. In this state, after deformation of the cornea is fixed, a riboflavin solution in a reservoir part integrally formed on the side of the contact lens that is not in contact with the cornea of the patient is infiltrated into the cornea from the outer side of the contact lens by iontophoresis action via a communication hole provided so as to penetrate through the contact lens, and the cornea is irradiated with UV rays via the contact lens after infiltration. The curvature of the curve of the convex part or the concave part may be set by anticipating the return of corneal deformation due to spring back of the eyeball (elongation of ocular axial length) when the contact lens is removed before infiltration of a riboflavin solution. Also, irradiation uses ultra violet A (UVA) wave that is known to be less harmful, but ultra violet B (UVB) wave may be irradiated simultaneously therewith or thereafter.

A working electrode has the same polarity as that of a riboflavin solution. When a DC current is applied, the riboflavin solution is repelled from the working electrode and attracted to a non-working electrode, resulting in infiltrating into the cornea.

The present invention is also applied to the case where return of corneal deformation due to spring back of the eyeball (elastically restoring force) is not anticipated.

In actual treatment, a contact lens is changed stepwise so as to correct the eyesight to a desired level. Finally, by using a contact lens that forms a concavely curved surface with a curvature of $R_0$ on the cornea for obtaining desired eyesight, a riboflavin solution is allowed to infiltrate and, while the foregoing state is maintained, the cornea is irradiated with UV rays via the contact lens.

When the elastically restoring force of the eyeball is not considered, the above-described concavely curved surface with the curvature of $R_0$ is formed by the pressing region that is a convexly curved surface with a curvature of $R_s$.

The present embodiment is characterized in that, in the case of correcting myopia, $R_s=R_0+5.0D$ to $R_0+10.0D$ is set to hold true, where $R_0$ denotes the curvature of a concavely curved surface to be formed on the cornea, and $R_s$ denotes the curvature of the convexly curved surface of the pressing region.

In this equation, D denotes diopter, which is a unit of the refractivity of the eye. The above-mentioned value ranging from +5.0D to +10.0D represents the correction amount obtained by considering corneal deformation after crosslinking on the basis of the elastically restoring force of the eyeball and is deduced from many treatment examples performed by the present inventor. It was known that corneal deformation after crosslinking is caused by the elastically restoring force of the cornea. However, it was not known that the aforementioned corneal deformation is also caused by the elastically restoring force of the eyeball. This finding was made by the present inventor.

The foregoing is determined by the fact that the curvature $R_s$ is given by $R_s=R_0+\Delta R$, where $\Delta R$ denotes the rate of change in the curvature at the central part of the corneal dome caused by the elastic restoring force of the eyeball when the cornea of the patient is pressed in the pressing region, which has a convexly curved surface with a curvature of $R_s$, and thereafter pressing is released.

Furthermore, this embodiment is characterized in that the pressing region and the relief region in the case of correcting hyperopia are opposite of those in the case of correcting myopia. Also, $r_s=r_0-6.5D$ to $r_0-11.5D$ is set to hold true, where $r_0$ denotes the curvature of a convexly curved surface to be formed on the cornea, and $r_s$ denotes the curvature of a concavely curved surface of the relief region. Also in this equation, the above-mentioned value ranging from −6.5D to −11.5D is deduced from treatment examples.

The aforementioned case of correcting hyperopia is also on the basis of the fact that the curvature $r_s$ is given by $r_s=r_0-\Delta r$, where $\Delta r$ denotes the rate of change in the curvature of the cornea caused by the elastically restoring force of the eyeball at the central part of the corneal dome.

Also, the lens thickness at the position of the concave part constituting the relief region in regions other than the central lens part may be set to 0.3 mm or greater.

In addition, the reservoir part may be formed seamlessly and integrally on the outer side of the lens. In this manner, the task of attaching the reservoir part to the lens is unnecessary, and it is possible to prevent leakage of a riboflavin solution which occurs only when the reservoir part is mounted on the lens surface.

Also, by setting the lens thickness to a value at least twice or more greater than that of the conventional lens, UV rays entering through the lens surface repeats reflection a plurality of times within the lens and can be made uniform and incident on the cornea.

Also, in the contact lens for corrective corneal crosslinking, the outer diameter $D_1$ of the circumferential edge part of the contact lens for corrective corneal crosslinking is preferably greater than the average outer diameter $D_0$ at the outer circumferential edge of the human cornea by 3.0 to 5.0 mm. A UV-shielding film for shielding UV rays is preferably disposed on the side being in contact with the cornea in the annular region of the outer circumferential edge part from the position where the diameter is $D_0-3.0$ mm to $D_0-5.0$ mm up to the outermost circumference.

When the outer circumferential edge of the cornea (corneal limbus) where a pluripotent cell exists is crosslinked by UV irradiation during crosslinking, corneal regeneration becomes difficult. The UV-shielding film is directed to preventing the aforementioned crosslinking from occurring. A UV-shielding film is particularly effective when UV rays repeat reflection within the lens and made incident on the cornea.

As a material of the UV-shielding film for shielding UV rays, a material harmless to the cornea, for example, a gold thin film, a titanium thin film, a silver thin film, and the like may preferably be used.

When the UV-shielding film is disposed on the outer side of the contact lens, UV rays entering through the central part of the contact lens are reflected/diffracted inside and eventually reach the outer circumferential edge of the cornea. Thus, the UV-shielding film is disposed on the side being in contact with the cornea.

Example 1

As illustrated in FIG. 1, a contact lens for corrective corneal crosslinking (hereinafter referred to as "contact lens") 30 according to Example 1 of the present invention, which is used for correcting myopia, is mounted on a cornea 2 for use thereof.

The contact lens 30 is configured to include: a lens part 30A; and a reservoir part 12 formed seamlessly and integrally therewith.

The lens part 30A includes: a circular central lens region being in contact with the center of a corneal dome (the most protruding part on the front end surface of the cornea 2) when the contact lens is mounted on the cornea of a patient; and a ring-shaped region in a circular-ring shape surrounding the central lens region. The central lens region includes a pressing region 32 formed to project in a convexly curved shape at a position for pressing the corneal dome center. The ring-shaped region is a relief region 34 that is formed at a position surrounding the outer circumference of the pressing region 32 and includes an annular concave part whose cross section is in a concavely circular arc shape. The lens part 30A is further configured to include: an anchor region 38 that is disposed at a position surrounding the outer circumference of the relief region 34 and is shaped to follow an outline 36 (see FIG. 2) of the cornea 2 when the contact lens is mounted on the cornea 2; and a circumferential edge part 40 surrounding the outer circumference of the anchor region 38.

The reservoir part 12 includes a cylindrical circumferential wall 12A that is formed integrally and seamlessly with the lens part 30A, on the outer side of the lens, of the relief region 34 including an annular concave part. The reservoir part 12 is constituted of the same material as that of the lens part 30A.

A working electrode 14 is constituted of a strip-shaped conductive material, such as a gold thin film or a conductive resin, formed in a cylindrical shape on the inner circumferential surface of the reservoir part 12. A non-working electrode 16 includes, for example, a conductive rubber and is adhered to the skin of a human body by a conductive tackiness agent, whereby current flow is possible.

The polarity of the working electrode 14 is the same as that of a riboflavin solution. In this case, it is cationic.

The cornea 2 in a state where the cornea 2 is corrected by the contact lens 30 is illustrated.

The lens thickness of the contact lens 30 of Example 1 is made thicker than that of a conventional contact lens 5A illustrated by a two-dot chain line in FIG. 1. The lens thickness at the lens center 30C is 0.3 mm or greater and 1.0 mm or smaller. When the lens strength needs to be increased, the lens thickness at the lens center may be 0.4 mm or greater and 1.0 mm or smaller.

The thickness of the bottom surface region at the concave part of the relief region is thinnest in the conventional contact lens 5A, except for the peripheral part. In Example 1, the lens thickness of a bottom surface 34A region of the annular concave part constituting the relief region 34 is the distance between the bottom surface 34A and a bottom surface 12B of the reservoir part 12, which is identical to the thickness of the central lens part. However, 0.3 mm is sufficient for this thickness.

A cornea infiltration device 10 is disposed outside the reservoir part 12 (on the side opposite to an eyeball 1).

The cornea infiltration device 10 is configured to include: the cylindrical reservoir part 12 that is formed integrally and seamlessly on the outer side of the contact lens 30 so as to correspond to the central part of the cornea 2 of the eyeball 1 of the patient; the working electrode 14 formed on the inner circumferential surface of the reservoir part 12; the non-working electrode 16 that is attached to patient skin near the eyeball 1; and a battery 13A and a switch 13B that are disposed between the working electrode 14 and the non-working electrode 16.

In FIG. 1, a numeral 3 denotes a crystalline lens, 6A denotes a UVA irradiation LED, 6B denotes a UVB irradiation LED, and a numeral 19 denotes a syringe for dropping a riboflavin solution from above the reservoir part 12.

Figure 2:
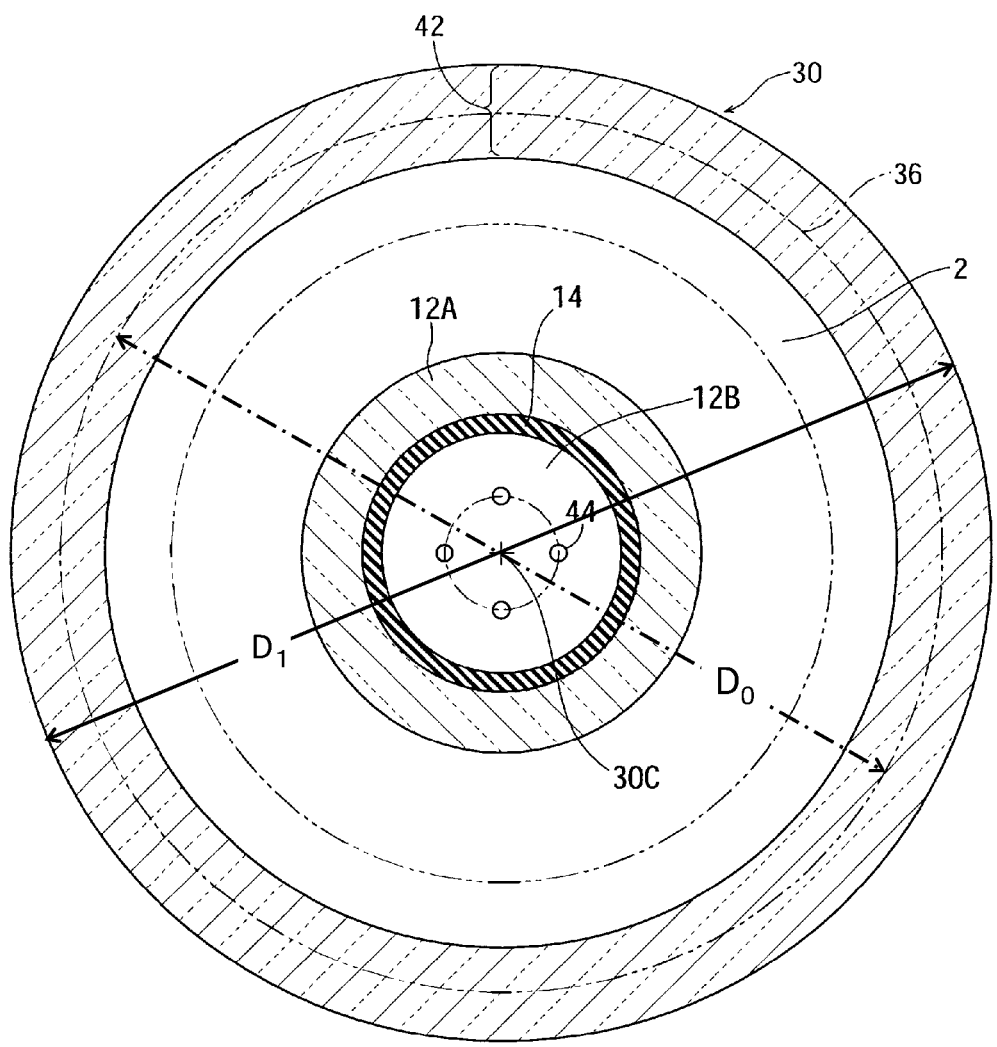
FIG. 2 is a plan view taken along a II-II line of FIG. 1, schematically illustrating the contact lens for corrective corneal crosslinking for correcting myopia.

As illustrated in FIG. 2, the lens part 30A is provided with communication holes 44 for communication between the inside of the reservoir part 12 and the pressing region 32. The communication holes 44 are disposed at four positions on the same virtual circle surrounding the center of the lens part 30A (lens center 30C) at equal intervals (equiangular interval of 90°) and penetrate through the pressing region 32 in the lens thickness direction.

The inner diameter of the reservoir part 12 is sized so as to surround the four communication holes 44 and the outer circumference of the pressing region 32. In FIG. 1, the conventional contact lens for myopia correction (hereinafter referred to as "conventional lens") 5A is indicated by a two-dot chain line. This conventional contact lens for myopia correction 5A includes a pressing region (with a convexly curved surface with a curvature of $R_0$) for forming a concavely curved surface with a curvature of $R_0$ in order to obtain a target naked eye vision of the patient.

As the solid line in FIG. 1 indicates, the pressing region 32 of the contact lens 30 of Example 1 projects toward the direction of the cornea 2 when compared with the conventional lens 5A. In contrast, the depth of the relief region 34 is greater than that of the relief region 7A of the conventional lens 5A to be formed as the annular concave part. Furthermore, the circumferential edge part 40 is greater than the circumferential edge part of the conventional lens 5A and extends along the outline 36 of the cornea 2.

In this case, $R_s = R_0 + 5.0D$ to $R_0 + 10.0D$ is set to hold true, where $R_s$ denotes the curvature of the convexly curved surface of the pressing region 32 of Example 1, and $R_0$ denotes the curvature of the convexly curved surface of the conventional lens 5A.

The curvature $R_0$ is the curvature of a concavely curved surface to be formed on the cornea 2 when at least one of the naked eye vision or keratoconus cornea of the patient is corrected. When the cornea of a patient is pressed in a pressing region with a convexly curved surface with a curvature of $R_0$ and pressing is released, deformation occurs so that the curvature of the concavely curved surface decreases due to the elastic restoring force (spring back) of the eyeball at the central part of the corneal dome. Thus, in anticipation of the amount of this spring back, $R_s > R_0$ is set to hold true, and the curvature $R_s$ is given by $R_s = R_0 + \Delta R$, where $\Delta R$ denotes the spring back amount.

Specifically, the spring back amount differs depending on the patient, and $\Delta R$ is determined by trial and error. However, treatment examples have shown that the spring back amount can be determined by approximating $\Delta R$ so that the curvature is given by $R_s = R_0 + 5.0D$ to $R_0 + 10.0D$.

As illustrated in FIGS. 1 and 2, an outer diameter $D_1$ of the circumferential edge part 40 of the contact lens 30 is greater than an average outer diameter $D_0$ of the human cornea at the outer circumferential edge thereof by 3.0 to 5.0 mm. A UV-shielding film 42 for shielding UV rays is disposed on the side being in contact with the cornea 2 in an annular region of the circumferential edge part 40 from the position where the diameter is $D_0 - 3.0$ mm to $D_0 - 5.0$=up to the outermost circumference. This UV-shielding film 42 is preferably a thin film made of a material that does not cause damage when being in contact with the cornea 2, such as Au, Ti, or Ag.

As illustrated in FIG. 2, when the UV-shielding film 42 is formed, the circumferential edge part 40 of the cornea 2 can maintain a pluripotent cell for cornea regeneration without being damaged by UV irradiation during crosslinking.

A description will now be given of the process of fixing the cornea 2 by crosslinking in a state where the contact lens 30 is used for correction.

Firstly, the contact lens 30, whose outer side is mounted with the cornea infiltration device 10, is attached to the cornea 2 of a patient, and the cornea 2 is corrected according to the shapes of the pressing region 32 and the relief region 34 on the inner side of the contact lens 30.

Subsequently, without changing the aforementioned correction state, i.e., in a state where the contact lens 30 is not removed, a riboflavin solution is injected into the reservoir part 12. Then, a current is supplied from the battery 13A to the region between the working electrode 14 and the non-working electrode 16.

Since the polarity of the riboflavin solution is the same as that of the working electrode 14, the riboflavin solution repels therefrom and moves toward the non-working electrode 16, i.e., the cornea 2, by iontophoresis action.

In this case, the communication holes 44 are provided between the reservoir part 12 and the surface of the cornea 2. The riboflavin solution in the reservoir part 12 passes through the communication holes 44, readily reaches the surface of the cornea 2, and infiltrates into the cornea 2.

In this process, since the reservoir part 12 is formed integrally with the lens part 30A, the riboflavin solution in the reservoir part 12 does not leak through the boundary therebetween to the lens surface, and thus the entire amount of the riboflavin solution reaches the surface of the cornea 2. Accordingly, unlike the conventional operation, a physician does not frequently blotting up a leaked riboflavin solution.

After the riboflavin solution infiltrates into the cornea 2, without changing the state, the cornea 2 is irradiated with UV rays via the contact lens 30, so that collagen fibers constituting the cornea 2 are crosslinked. In this case, it is preferable that UV rays be irradiated mainly from the reservoir part 12.

In this Example, UVA from the UVA irradiation LED 6A is mainly irradiated. However, UVB from the UVB irradiation LED 6B may be irradiated either simultaneously with or after UVA irradiation. UVB is harmless when applied in a small quantity for a short period of time and can restrain the myopia progress.

Since the bottom part of the reservoir part 12 is a central lens region, the cornea 2 can be irradiated with UV rays through the bottom part.

For example, as illustrated in FIG. 1, a UV incident region 31 may be provided in the region of the outer lens surface along the outer periphery of the reservoir part 12 and a remaining region of the outer lens surface may be coated with a UV reflection film 31A, so that UV rays are irradiated from the UV incident region 31. The UV incident region 31 is formed in a circular-ring shape to surround the reservoir part 12 so that UV rays are incident on one or a plurality of positions. The UV reflection film 31A is constituted of a material, such as Au, Ag, Cu, or Ti. When the UV reflection film 31A is disposed in the reservoir part 12, the film 31A can also serve as a working electrode.

In the UV incident region 31, UV rays are made incident on and enter the lens part 30A so as to be orthogonal to the lens surface. The UV rays thus having entered travel straight and are made incident on the cornea 2 from the opposite side of the lens. Also, a part thereof is internally reflected and diffracted, reflected by the UV reflection film 31A, output through the inner lens surface, and made incident on the cornea 2.

On the side of the contact lens 30 being in contact with the cornea 2, the UV-shielding film 42 is formed to cover the circumferential edge part 40, and thus UV rays do not reach the cornea 2. Accordingly, the pluripotent cell in the cornea 2 on the inner side of the circumferential edge part 40 is not damaged.

When the contact lens 30 is removed upon completion of UV irradiation, the cornea 2 is fixed in the shape formed by the pressing region 32 and the relief region 34.

The central part of the cornea 2 is projected by the elastic restoring force of the eyeball after removal of the contact lens 30. Since the curvature $R_s$ of the convexly curved surface of the pressing region 32 is set in anticipation of the spring back amount in advance, the curvature of the concavely curved surface formed on the cornea 2 is $R_0$ even after spring back occurs.

Example 2

Figure 3:
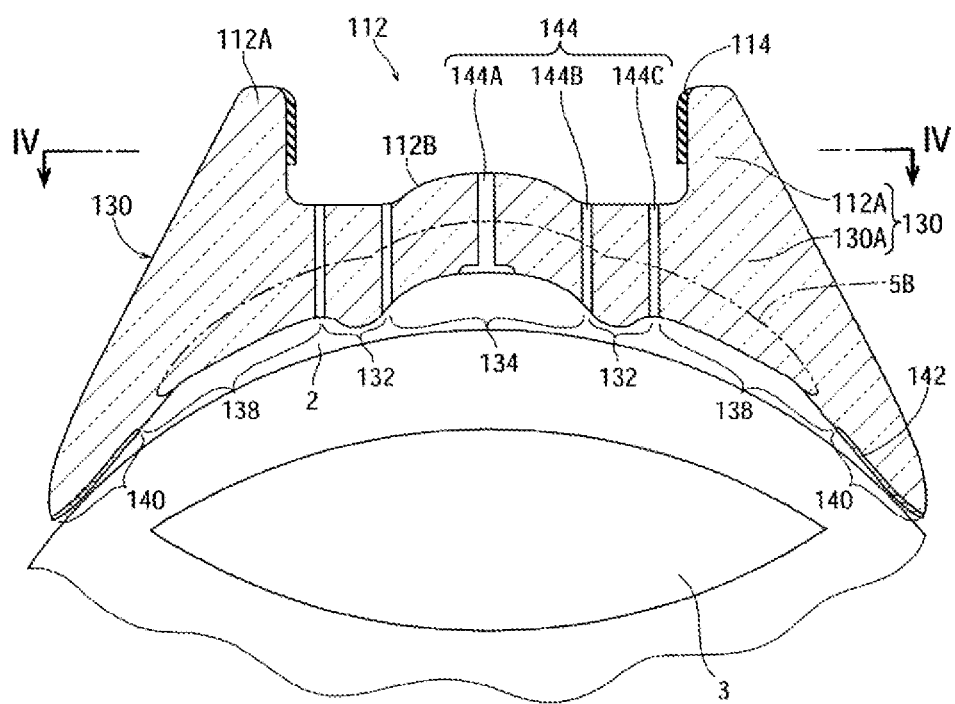
FIG. 3 is a cross-sectional view schematically illustrating a contact lens for corrective corneal crosslinking for correcting hyperopia according to Example 2 of the present invention.

A description will now be given of a contact lens for hyperopia correction 130 according to Example 2, which is illustrated in FIG. 3. In FIG. 3, the two-dot chain line indicates a conventional contact lens for hyperopia correction 5B.

The contact lens for hyperopia correction 130 of Example 2 is configured such that the concave and convex portions of the pressing region and the relief region of the contact lens 30 of FIG. 1 are exchanged for each other. Specifically, the central lens region is a relief region 134, and the ring-shaped region is a pressing region 132.

The relief region 134 in a lens part 130A in this contact lens for hyperopia correction 130 is formed in a concavely curved shape at a position being in contact with the central part of the corneal dome when the contact lens is mounted on the cornea 2. In addition, the pressing region 132 includes an annular convex part that is formed at a position surrounding the outer circumference of the relief region 134 and whose cross section is in a convexly circular arc shape.

Figure 4:
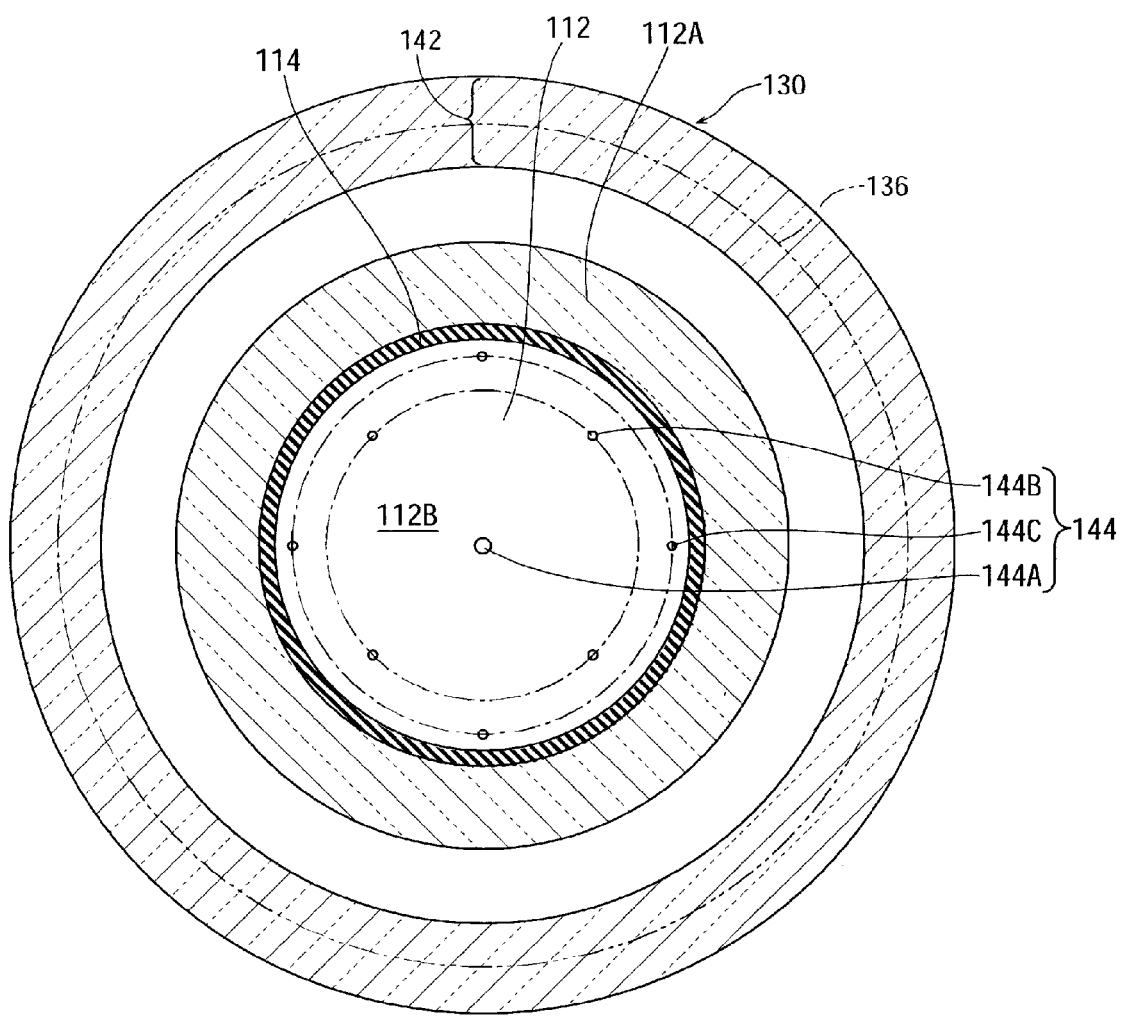
FIG. 4 is a plan view taken along a IV-IV line of FIG. 3, schematically illustrating the contact lens for corrective corneal crosslinking for correcting hyperopia.

Furthermore, an anchor region 138 is disposed at a position surrounding the outer circumference of the pressing region 132 and shaped to follow an outline 136 (see FIG. 4) of the cornea when the contact lens is mounted on the cornea 2. A circumferential edge part 140 is configured to surround the outer circumference of the anchor region 138. A numeral 142 in FIG. 3 denotes a UV-shielding film.

In the contact lens for hyperopia correction 130 according to Example 2, a total of nine communication holes 144 penetrating through the contact lens for hyperopia correction 130 in the thickness direction thereof are formed between the inside of the reservoir part 112 and the surface on the cornea 2 side.

A central communication hole 144A having a larger inner diameter than those of the other communication holes is disposed at the central position of the contact lens for hyperopia correction 130. Four intermediate communication holes 144B and four outer communication holes 144C are respectively formed on two concentric circles surrounding the central communication hole 144A (see FIG. 4). The intermediate communication holes 144B are disposed within the relief region 134 at positions adjacent to the side of the pressing region 132 close to the lens center. The outer communication holes 144C are disposed at positions adjacent to the side of the pressing region 132 opposite to the lens center (on the outside thereof).

Both the intermediate communication holes 144B and the outer communication holes 144C may be disposed at a plurality of, three or more, positions at equal intervals. When the intermediate communication holes 144B are disposed in the pressing region 132, the outer communication holes 144C do not need to be disposed.

The reservoir part 112 is formed so that the inner diameter thereof is set to form a concentric circle further outside the concentric circle on which the outer communication holes 144C are formed.

Also in this Example, the reservoir part 112 is formed integrally and seamlessly with the lens part 130A on the outer lens surface.

Moreover, the lens thickness of the lens part 130A of the contact lens 130 in Example 2 is thicker than that of the conventional contact lens 5B illustrated by a two-dot chain line in FIG. 3. The lens thickness of the central lens part, specifically, at the center of the relief region 134, is 0.3 mm or greater and 1.0 mm or smaller. In Example 2, the lens thickness of the relief region is thinnest, and the thicknesses of the other regions are thicker than that at the central lens part. When the lens strength needs to be increased, the lens thickness of the central lens part may be 0.4 mm or greater and 1.0 mm or smaller.

The contact lens for hyperopia correction 130 according to Example 2 is configured so that during eye vision correction, $r_s=r_0-6.5D$ to $r_0-11.5D$ is set to hold true, where $r_0$ denotes the curvature of a convexly curved surface to be formed on the cornea 2, and $r_s$ denotes the curvature of the concavely curved surface of the relief region 134.

This value is a correction amount considering a spring back amount $\Delta r$ caused by the elastic restoring force of the eyeball at the central part of the corneal dome when pressing of the contact lens for hyperopia correction 130 is released. This value is deduced from many treatment examples performed by the present inventor, and the curvature $r_s$ is given by $r_s=r_0-\Delta r$.

When this contact lens for hyperopia correction 130 is used to perform crosslinking for cornea correction, the same process as that of the contact lens for myopia correction 30 according to the above-described Example 1 is employed to perform the aforementioned crosslinking.

The working electrodes 14, 114 of the Examples 1 and 2 described above are formed on the inner circumferential surfaces of the reservoir parts 12, 112. These may be configured by disposing, for example, a light transmissive conductive film or a light transmissive thin metal film on the bottom surfaces 12B, 112B of the reservoir parts 12, 112, i.e., the surfaces of the lens parts.

Example 3

The contact lenses for corrective corneal crosslinking 30, 130 of the above-described Examples 1 and 2 are circular when the contact lenses are mounted on the cornea of the patient and seen from the front side. However, the present invention is not limited to the foregoing.

Figure 5:
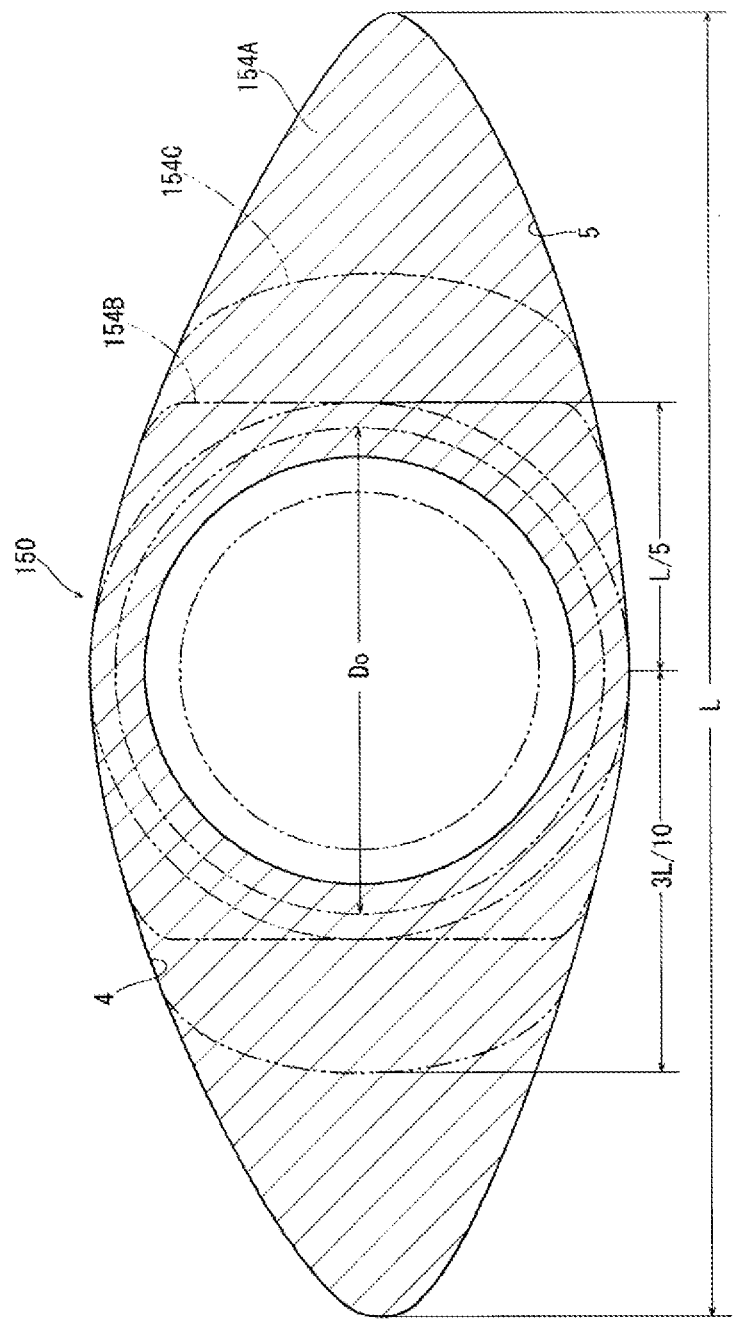
FIG. 5 is a plan view schematically illustrating a contact lens for corrective corneal crosslinking for correcting hyperopia according to Example 3 of the present invention.

As illustrated in FIG. 5, a contact lens for corrective corneal crosslinking 150 according to Example 3 is provided with an extension part 154A on both sides in a width direction of the circular shape of the contact lens for corrective corneal crosslinking 30 or 130. Specifically, the lens outer shape when the contact lens is mounted on the cornea of the patient and seen from the front side is configured to coincide with the shapes of the inner circumferences of an upper eyelid 4 and a lower eyelid 5 when the upper and lower eyelids 4 and 5 are opened. A reservoir part, communication holes, and the like are not illustrated in the figure.

In this configuration, the contact lens for corrective corneal crosslinking does not move vertically or horizontally or rotate with respect to the cornea center during crosslinking. Surgery can thus be stably performed.

The aforementioned extension part may be of any type as long as movement and rotation of the contact lens for corrective corneal crosslinking can be restrained. The length of the extension part in the width direction thereof may be set such that the length thereof in a state where the contact lens is in contact with the inner circumferences of scales 4,5 falls within a range of L/5 to L/2 in a width direction of the eye with respect to the eye center to the left or right side, where L denotes the entire width of the shapes of the inner circumferences of the upper and lower eyelids 4 and 5. For example, as illustrated by two-dot chain lines in FIG. 5, an extension part 154B with a width of L/5 or an extension part 154C with a width of 3 L/10 may be disposed to the left and right sides thereof.

The maximum thickness at the central lens part is set to 1.0 mm in the above Examples since sufficient strength can be achieved at a thickness of 1.0 mm and any greater thickness simply increases the lens weight.

Example 4

Of the aforementioned Examples 1 to 3, the production process of grinding and cutting out the contact lens for corrective corneal crosslinking of the Example 1 will be described.

Figure 6C:
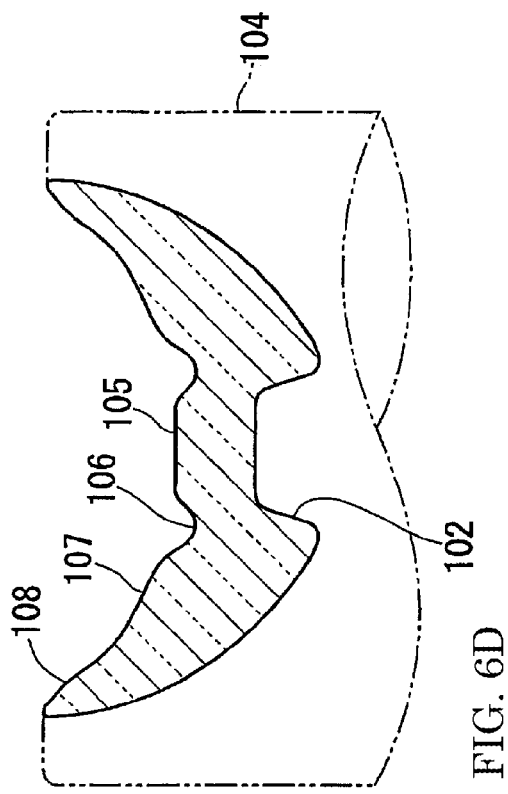
FIGS. 6B, 6C, and 6D are cross-sectional views schematically illustrating a process of grinding and cutting out a contact lens for corrective corneal crosslinking from a lens material.
Figure 6D:
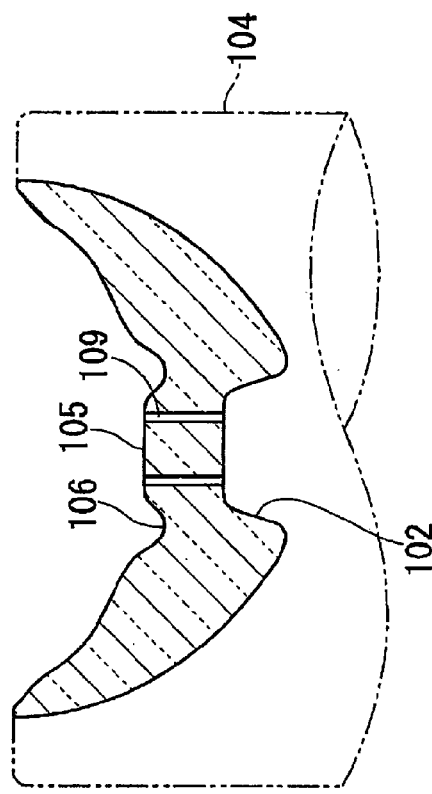
Figure 6A:
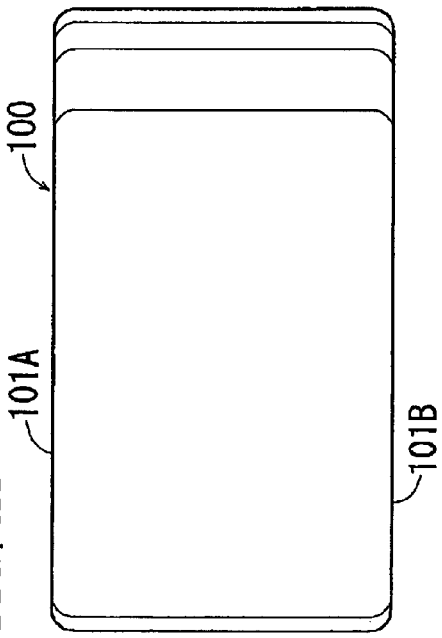
FIG. 6A is a perspective view schematically illustrating a process of grinding and cutting out a contact lens for corrective corneal crosslinking from a lens material.
Figure 6B:
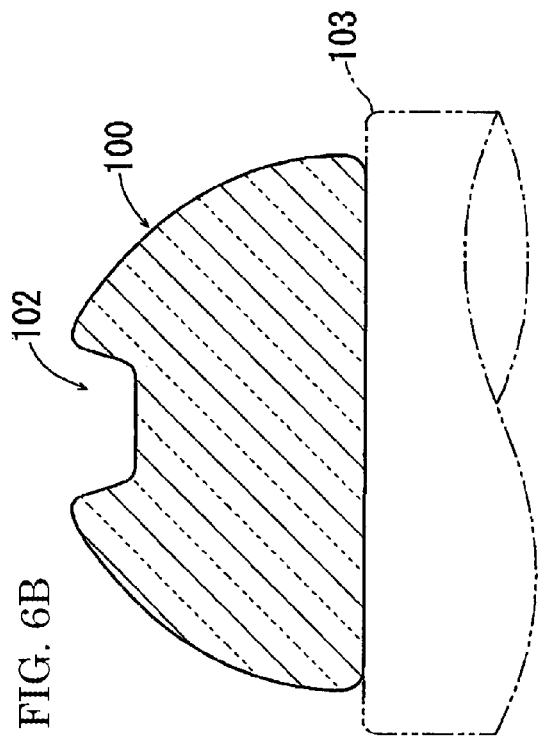

On one end surface 101A of a lens material 100 illustrated in FIG. 6A, which is referred to as a button, a reservoir part 102 as illustrated in FIG. 6B is first formed by grinding and cutting out. In this case, the lens material 100 is held on a holder 103 by an adhesive or a fixture. Next, as illustrated in FIG. 6C, the lens material 100 on the reservoir part 102 side thereof is held by a fixture 104. A pressing region 105, a relief region 106, an anchor region 107, and a circumferential edge part 108 are formed by grinding and cutting out an end surface 101B on the other side. Finally, as illustrated in FIG. 6D, communication holes 109 are formed by laser beam, drilling, etc. Grinding and cutout of the reservoir part 102 illustrated FIG. 6B exerts pressure on the outer side of the lens. Since this surface is not brought into contact with the cornea, it may be roughly ground.

Accordingly, in the steps illustrated in FIGS. 6C and 6D, there is no problem when this surface is damaged by a fixture during fixation of the contact lens.

Also, the pressing region 105 and the relief region 106 require precise polishing because these regions are brought into contact with the cornea. However, since the other side can be securely fixed, precise polishing is enabled.

As described above, the reservoir part 102 may be formed by performing an injection molding or the like in advance when the lens material 100 is produced.

INDUSTRIAL APPLICABILITY

The contact lens according to the present invention has high industrial applicability as a contact lens for corrective corneal crosslinking because the contact lens has high rigidity and high crack resistance and allows a riboflavin solution to quickly and reliably infiltrate into the cornea with little leakage when the cornea is fixed by crosslinking in a state where the corneal shape is corrected by the contact lens.

REFERENCE SIGNS LIST

1 . . . eyeball
2 . . . cornea
3 . . . crystalline lens
4 . . . upper eyelid
5 . . . lower eyelid
6A UVA (ultraviolet A wave) irradiation LED
6B UVB (ultraviolet B wave) irradiation LED
10 . . . cornea infiltration device
12, 102, 112 . . . reservoir part
12A, 112A . . . circumferential wall
12B, 112B . . . bottom surface
13A . . . battery
13B . . . switch
14, 114 . . . working electrode
16 . . . non-working electrode
19 . . . syringe 30, 130, 150 . . . contact lens for corrective corneal crosslinking (contact lens)
30A, 130A . . . lens part
30C . . . lens center
31 . . . UV incident region
31A . . . UV reflection film
32, 105, 132 . . . pressing region
34, 106, 134 . . . relief region
36, 136 . . . outline
38, 107, 138 . . . anchor region
40, 108, 140 . . . circumferential edge part
42, 142 . . . UV-shielding film
44, 109, 144 . . . communication hole
100 . . . lens material
101A, 101B . . . end surface
103 . . . holder
104 . . . fixture
144A . . . central communication hole
144B . . . intermediate communication hole
144C . . . outer communication hole
154A, 154B, 154C . . . extension part

The invention claimed is:

1. A contact lens for corrective corneal crosslinking, comprising:
   a UV transmitting material;
   a relief region comprising a concave part and a pressing region comprising a convex part that are formed on a side of the contact lens that is configured to be in contact with a cornea of a patient; and
   a lens part and a reservoir part, wherein:
   the contact lens is configured to correct at least one of a naked eye vision and keratoconus cornea by pressing the relief region and the pressing region to the cornea to change a shape of the cornea;
   the lens part comprises, on the side thereof configured to be in contact with the cornea of the patient, a circular central lens region that is located at a position configured to be in contact with a corneal dome center when the contact lens is mounted on the cornea, and a ring-shaped region in a circular-ring shape surrounding the central lens region; one of the central lens region and the ring-shaped region constitutes the pressing region or the relief region and the other constitutes the relief region or the pressing region;
   the reservoir part comprises the same material as that of the lens part, is disposed and formed to project seamlessly and integrally with the lens part at an outside position in a lens thickness direction in the central lens region, is configured to store a riboflavin solution for corrective conical crosslinking, and has a working electrode that is disposed at a position being in contact with the riboflavin solution and has the same polarity as that of the riboflavin solution; and
   the lens part has at least one communication hole for communication between an inside of the reservoir part and the central lens region, has a lens thickness in a range of from 0.3 mm to 1.0 mm in the central lens region, and enables infiltration of the riboflavin solution into a corneal tissue by iontophoresis.

2. The contact lens for corrective conical crosslinking according to claim 1, wherein
   the reservoir part comprises a cylindrical circumferential wall that is formed integrally and seamlessly with the lens part on an outer side of the contact lens, of the ring-shaped region.

3. The contact lens for corrective conical crosslinking according to claim 2, wherein
   a UV incident region is provided to the circumferential wall, the UV incident region allowing UV rays to enter an inside of the contact lens.

4. The contact lens for corrective conical crosslinking according to claim 1, wherein
   a UV incident region is provided in an outer circumference region surrounding the reservoir part on an outer side of the contact lens, the UV incident region allowing UV rays to enter an inside of the contact lens.

5. The contact lens for corrective conical crosslinking according to claim 1, wherein:
   the central lens region is the pressing region configured to project in a convexly curved shape at a position for pressing the corneal dome center when the contact lens is mounted on the cornea and to form a concavely curved surface on the cornea; and
   the ring-shaped region is the relief region that is formed at a position surrounding an outer circumference of the pressing region and comprises an annular concave part whose cross section has a concavely circular arc shape.

6. The contact lens for corrective corneal crosslinking according to claim 5, wherein
   the at least one communication hole is a plurality of communication holes disposed at a plurality of positions on a same virtual circle surrounding a center of the contact lens in the pressing region to penetrate therethrough in the lens thickness direction.

7. The contact lens for corrective corneal crosslinking according to claim 6, wherein
   the plurality of communication holes are disposed at equiangular intervals on the same virtual circle.

8. The contact lens for corrective corneal crosslinking according to claim 1, wherein:
   the central lens region is the relief region that is formed in a concavely curved shape at a position being in contact with the corneal dome center when the contact lens is mounted on the cornea, and is configured to form a convexly curved surface on the cornea; and
   the ring-shaped region is the pressing region that is formed at a position surrounding an outer circumference of the relief region and comprises an annular convex part whose cross section has a convexly circular arc shape.

9. The contact lens for corrective conical crosslinking according to claim 8, wherein
   the reservoir part comprises a cylindrical circumferential wall that is formed integrally and seamlessly with the lens part on an outer side of the contact lens, of the annular convex part to surround the at least one communication hole.

10. The contact lens for corrective conical crosslinking according to claim 9, wherein
    the at least one communication hole comprises one communication hole disposed at a position of center of the contact lens, and a plurality of communication holes on at least one same virtual circle surrounding the center of the contact lens at equiangular intervals.

11. The contact lens for corrective conical crosslinking according to claim 8, wherein
    the at least one communication hole comprises one communication hole disposed at a position of a center of the contact lens, and a plurality of communication holes on at least one same virtual circle surrounding the center of the contact lens at equiangular intervals.

12. The contact lens for corrective conical crosslinking according to claim 11, wherein the plurality of communication holes are disposed on the at least one same virtual circle within the relief region at positions adjacent to a side of the pressing region close to the center of the contact lens.

13. The contact lens for corrective conical crosslinking according to claim 8, wherein the reservoir part is disposed on an outer side of the contact lens in a lens thickness direction of the relief region and the pressing region, and an outer communication hole for communication between the inside of the reservoir part and a position of the outer circumference of the pressing region is further disposed.

14. The contact lens for corrective conical crosslinking according to claim 1, wherein any of a light transmissive conductive film and a light transmissive thin metal film is disposed on a surface of the contact lens at a position being in contact with the riboflavin solution in the reservoir part to serve as the working electrode.

15. The contact lens for corrective conical crosslinking according to claim 1, wherein a contact lens outer shape when the contact lens is mounted on the cornea of the patient and seen from a front side coincides with shapes of inner circumferences of an upper eyelid and a lower eyelid of the patient when the upper and lower eyelids are opened such that a length of the contact lens where the contact lens is in contact with the inner circumferences of the eyelids falls within a range of L/5 to 3L/10 in a width direction with respect to an eye center to a right or left side, where L denotes an entire width of the inner circumferences in a horizontal direction.

16. A method for producing the contact lens for corrective corneal crosslinking according to claim 1, comprising:

forming the reservoir part on one end surface of a circular plate lens material; and then grinding the pressing region and the relief region on the other end surface, while the reservoir part is held, to form the lens part seamlessly and integrally with the reservoir part and a surface of the lens part to be in contact with the cornea of a patient.

* * * * *